(12) United States Patent
Zheng (10) Patent No.: US 7,293,369 B2
(45) Date of Patent: Nov. 13, 2007

(54) APPLIANCES HAVING BUILT-IN WATER DISPENSER

(75) Inventor: Yu Zheng, Walnut, CA (US)

(73) Assignee: Patent Category Corp., Walnut, CA (US)

( * ) Notice: Subject to any disclaimer, the term of this patent is extended or adjusted under 35 U.S.C. 154(b) by 0 days.

(21) Appl. No.: 11/023,725

(22) Filed: Dec. 28, 2004

(65) Prior Publication Data

US 2006/0137209 A1   Jun. 29, 2006

(51) Int. Cl.
*F26B 25/06* (2006.01)
*A61M 16/00* (2006.01)
*A61H 33/06* (2006.01)

(52) U.S. Cl. ............................ 34/201; 34/72; 392/394; 392/405

(58) Field of Classification Search .................. 34/201, 34/218, 72; 392/390, 394, 395, 405; 261/142, 261/153, DIG. 65; 236/44 R
See application file for complete search history.

(56) References Cited

U.S. PATENT DOCUMENTS

| 1,656,414 | A | * | 1/1928 | Braemer ................... 236/44 R |
| 2,075,862 | A | * | 4/1937 | Myers ........................ 261/142 |
| 3,306,010 | A | * | 2/1967 | Garofalow et al. ......... 392/405 |
| 4,529,867 | A | * | 7/1985 | Velnosky et al. ........... 392/405 |
| 4,810,854 | A | * | 3/1989 | Jursich et al. .............. 392/405 |
| 6,220,579 | B1 | * | 4/2001 | Chen .......................... 261/142 |

* cited by examiner

*Primary Examiner*—Jiping Lu
(74) *Attorney, Agent, or Firm*—Raymond Sun (57) ABSTRACT

An appliance is provided with a water dispenser. A fan or heater assembly, a hair dryer assembly, and a brush assembly are disclosed. Each of these assemblies includes a water dispenser incorporated therein.

4 Claims, 9 Drawing Sheets

APPLIANCES HAVING BUILT-IN WATER DISPENSER

BACKGROUND OF THE INVENTION

1. Field of the Invention

The present invention relates to various appliances, and in particular, to appliances having a built-in water dispenser that dispenses water to enhance the use of the appliance.

2. Description of Related Art

Numerous conventional appliances are readily available in the marketplace. Fans and heaters are provided to improve comfort and the living environment inside homes. Hair dryers and brushes are provided to help individuals style their hair.

SUMMARY OF THE INVENTION

It is an objective of the present invention to provide a heater or fan with a built-in humidifier and water spray.

It is another objective of the present invention to provide a hair dryer with a built-in water spray.

It is yet another objective of the present invention to provide a brush with a built-in water spray.

The objectives of the present invention can be accomplished by providing an appliance that has a water dispenser. In one embodiment of the present invention, a fan or heater assembly has a base portion, a blower portion that blows air into the environment, a water tank that contains water, and water outlets fluidly coupled to the water tank for dispensing water into the environment.

According to another embodiment of the present invention, a hair dryer assembly has a handle portion, a blower portion that blows air into the environment, a water tank, a plurality of nozzles fluidly coupled to the water tank, and a pump system that delivers water from the water tank to the nozzles for dispensing water into the environment.

According to yet another embodiment of the present invention, a brush assembly has a handle portion, and a water spray portion secured to the handle portion, the water spray portion having a tube with nozzles provided about the body. The brush assembly also has a water tank that is fluidly coupled to the nozzles, a pump system that delivers water from the water tank to the nozzles for dispensing water into the environment, and a brush portion that is coupled to the tube.

DESCRIPTION OF THE PREFERRED EMBODIMENTS

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

Figure 1:
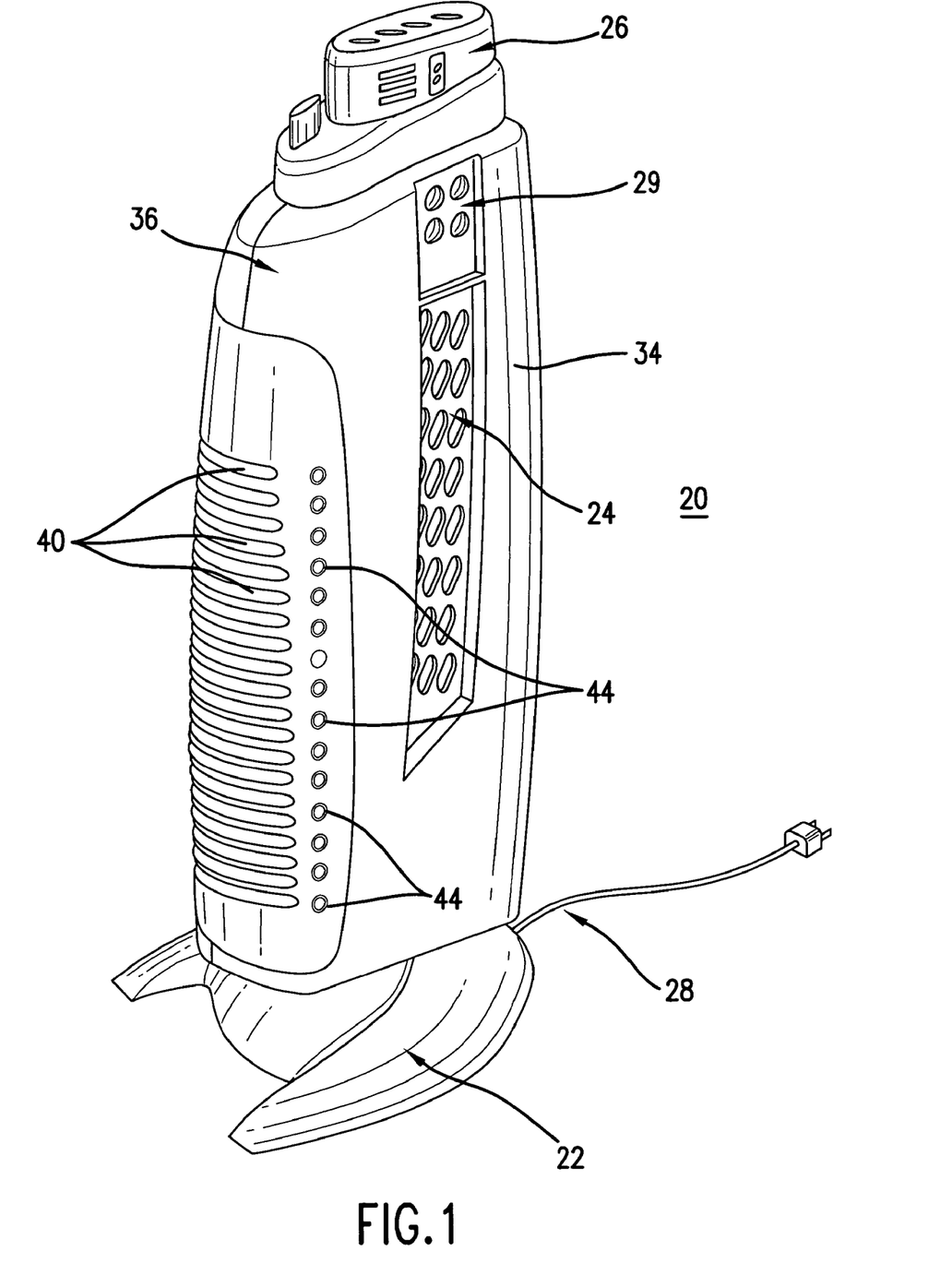
FIG. 1 is a perspective view of a heater assembly according to one embodiment of the present invention.
Figure 2:
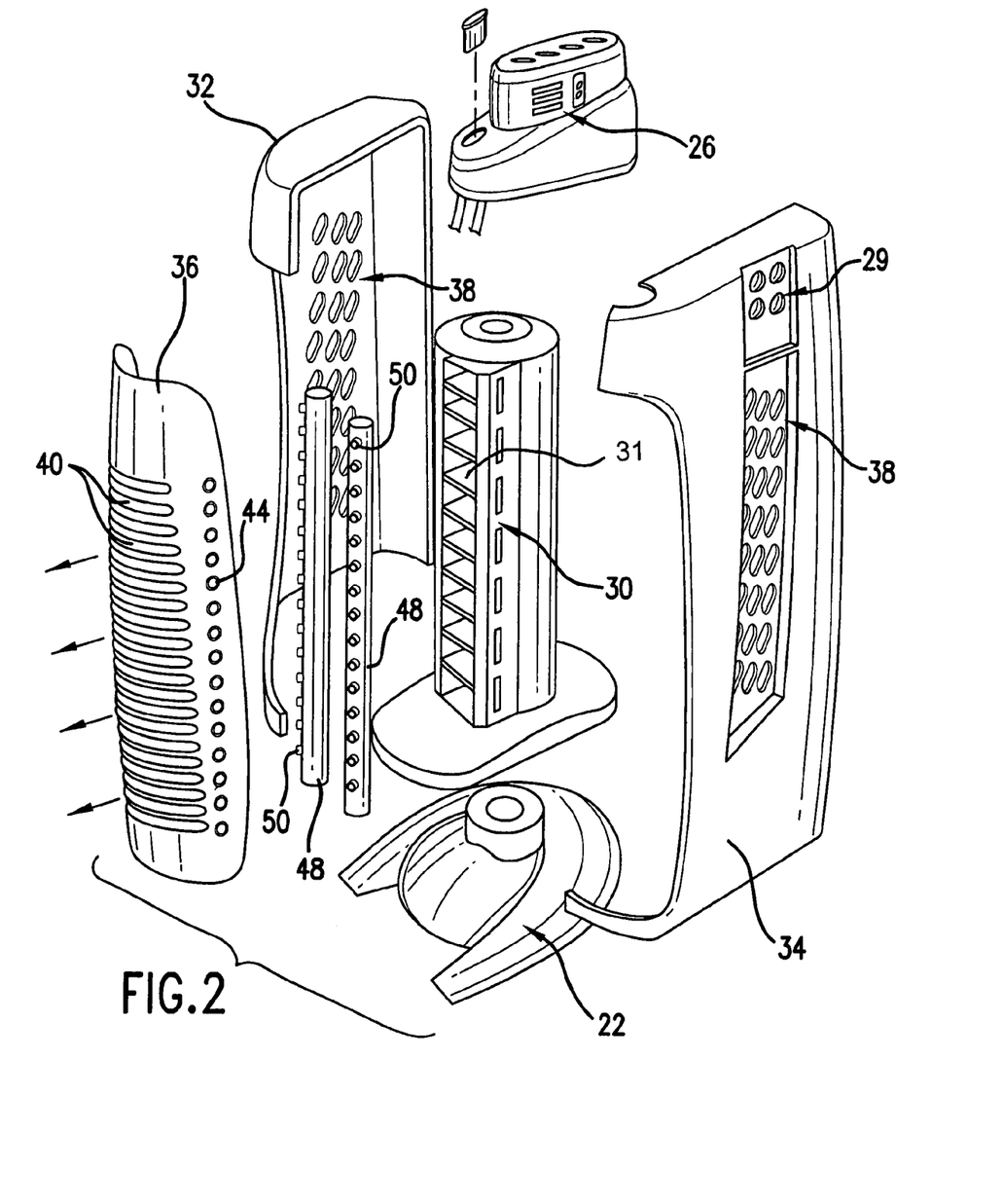
FIG. 2 is an exploded perspective view of the heater assembly of FIG. 1.
Figure 3:
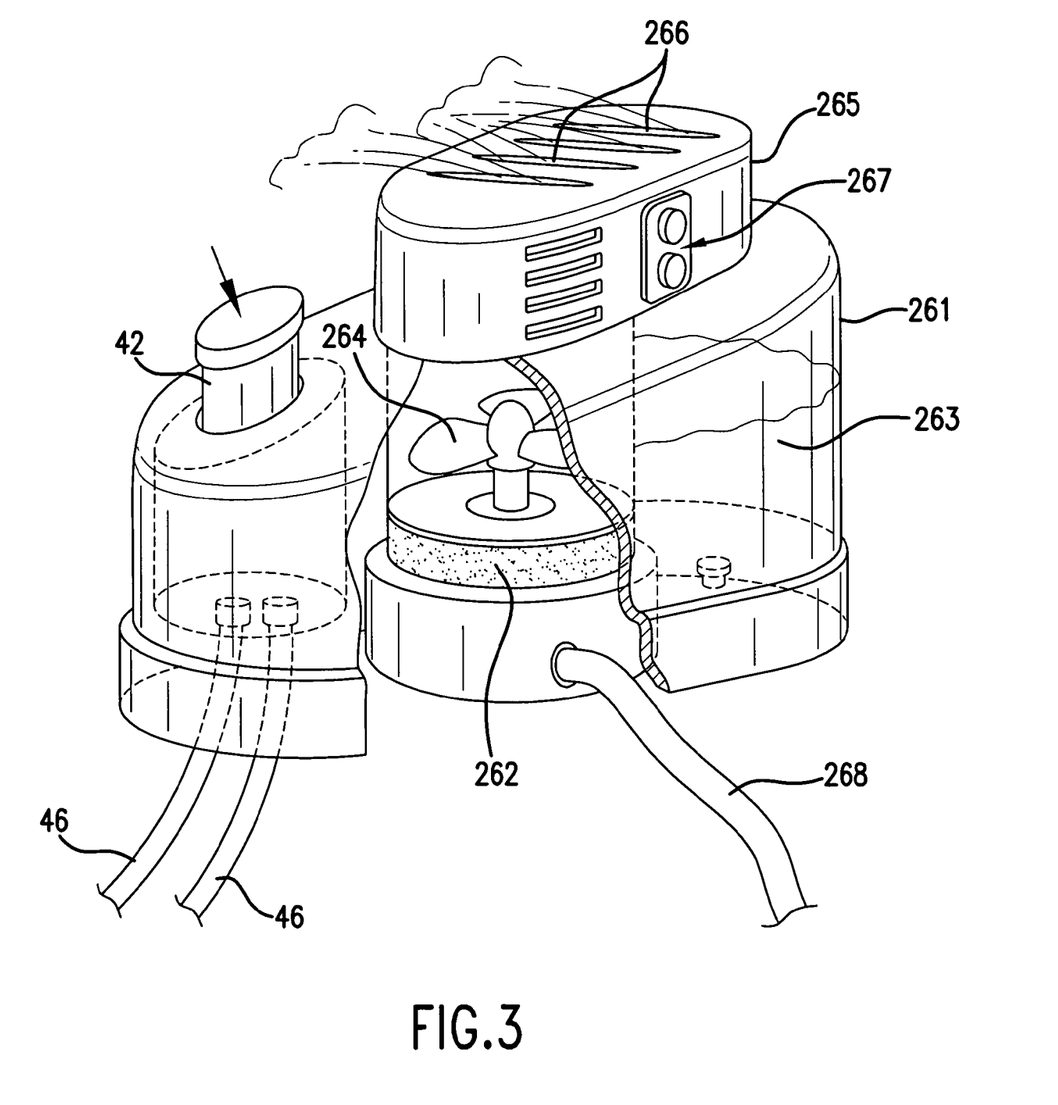
FIG. 3 is a perspective view of the humidifier portion of the heater assembly of FIG. 1.

FIGS. 1-3 illustrate one embodiment of a heater assembly 20 according to the present invention. The heater assembly 20 has a base portion 22, a blower portion 24 and a humidifier portion 26. The base portion 22 houses the circuit board, power system, and other electronics for the heater assembly 20. The circuit board, power system and electronics can be the same as for any of the conventional heater assemblies that are currently available in the marketplace, and will not be described in further detail. A power cord 28 extends from the base portion 22 to provide power from an external power source. A control panel 29 can be provided on a side wall 34 of the blower portion 24 for controlling the operation of the assembly 20.

The blower portion 24 has a heater 30 and a blower 31 that is housed inside a housing that is made up of two side walls 32, 34 and a front wall 36 that are attached together to form a hollow interior space that receives and holds the heater 30. Air inlets 38 are provided in the side walls 32, 34 through which air can be drawn for use by the heater 30. Air outlets 40 are provided in the front wall 36 through which heated air can be ejected. In addition, water outlets 44 are provided in the front wall 36 through which water can be ejected.

Referring to FIGS. 2-3, the humidifier portion 26 can be any conventional humidifier that is provided at the top of the walls 32, 34, 36. The humidifier portion 26 includes the components of a conventional humidifier, including a housing 261 that houses a filter 262, a water tank 263, a motor (not shown) and a blower or fan 264. A mist section 265 is provided above the housing 261, and has mist outlets 266 through which cool or warm mist can be introduced into the environment. The motor can be retained in either the mist section 265 or the housing 261. A control panel 267 can be provided on either the mist section 265 or the housing 261 to allow for control of the humidifier separate from control for the heater 30. In addition, a power cord 268 extends from the housing 261 to allow power to be provided separately to the humidifier and the heater 30. Alternatively, wiring (not shown) can extend through the blower portion 24 to couple the circuit board and electronics in the base portion 22 to the motor in the humidifier portion 26.

A pump 42 is provided in the housing 261 of the humidifier portion 26. The pump 42 can be embodied in the form of any conventional negative-pressure pump, and functions to deliver water from the water tank 263 to at least one water tube 46 which extends from the humidifier portion 26 into the interior of the blower portion 24. Each water tube 46 is fluidly coupled to a corresponding water conduit 48 that is located at a position that is adjacent to the front wall 36. Water outlets 50 are provided on the conduit(s) 48 at locations adjacent to the water outlets 44.

In use, a user can turn on the heater 30 by controlling the control panel 29, such as by turning on one or more switches. The heater 30 emits warm air through the air and water outlets 40. In one embodiment, the blower portion 24 rotates in a reciprocal manner about the fixed base portion 22 to disperse the heat. If the user desires to provide a less dry (i.e., slightly more humid) environment, the user can turn on the humidifier by controlling the control panel 267 on the mist section 265. The user can additionally (and optionally) actuate the pump 42 (by pressing) to cause water to be pumped from the water tank 50 via the tube(s) 46 and conduit(s) 48, and ejected through the water outlets 50 and 44. Thus, the user can operate the heater 30 and the humidifier portion 26 separately and independently from each other. In other words, the user can operate the humidifier portion 26 alone, the heater 30 alone, or both the heater 30 and the humidifier portion 26.

Even though FIGS. 1-3 illustrate a heater assembly 20, the heater 30 can be a conventional cooling fan, in which case the blower portion 24 would be blowing cool air as opposed to warm air. The construction, structure and features of conventional blower portions used for fan assemblies are well-known to those skilled in the art.

In addition, although the humidifier portion 26 is illustrated as being provided above the blower portion 24, it is also possible to position the humidifier portion 26 below the blower portion 24, or to one side of either of the side walls 32 or 34.

Figure 4:
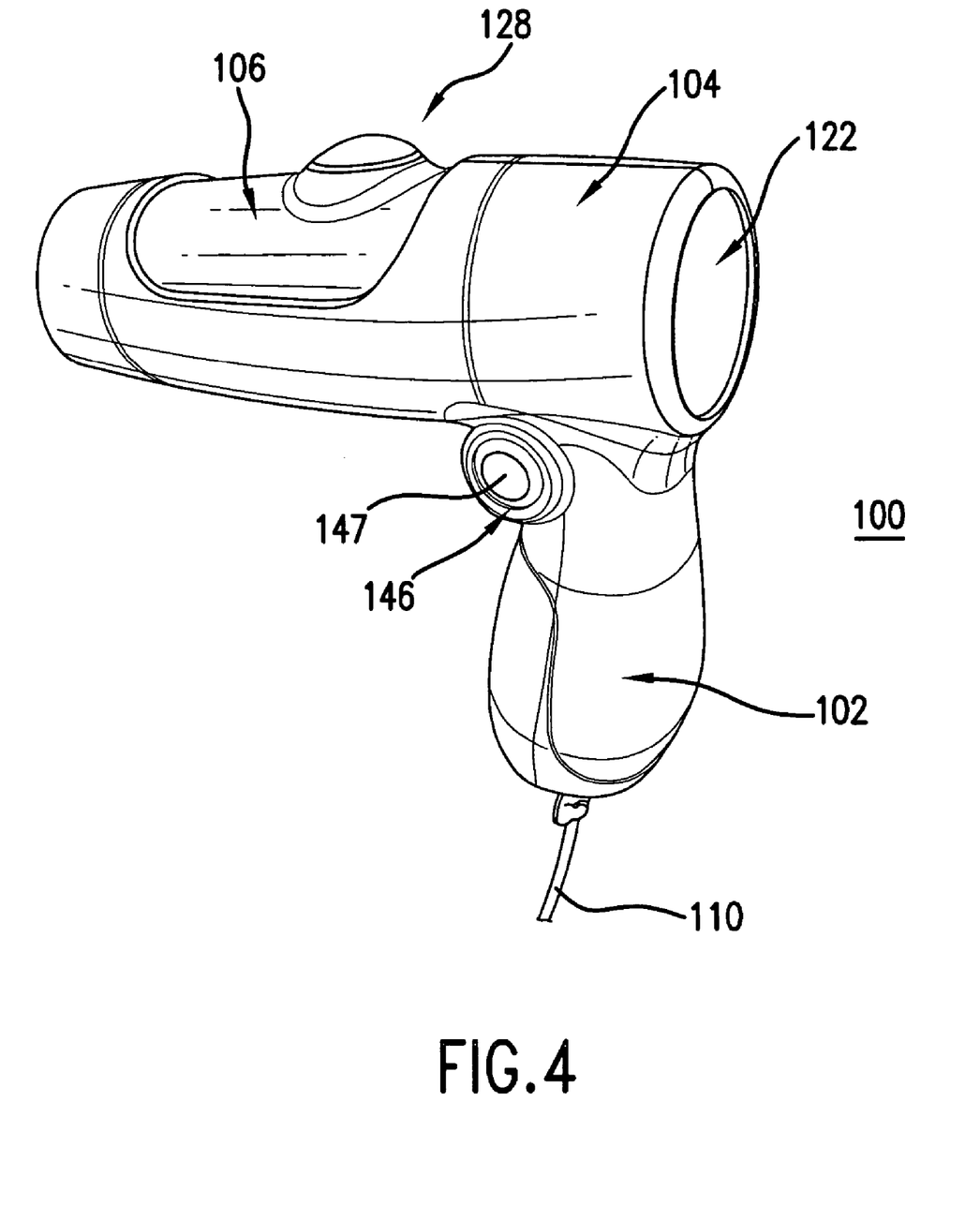
FIG. 4 is a perspective view of a hair dryer assembly according to one embodiment of the present invention.
Figure 5:
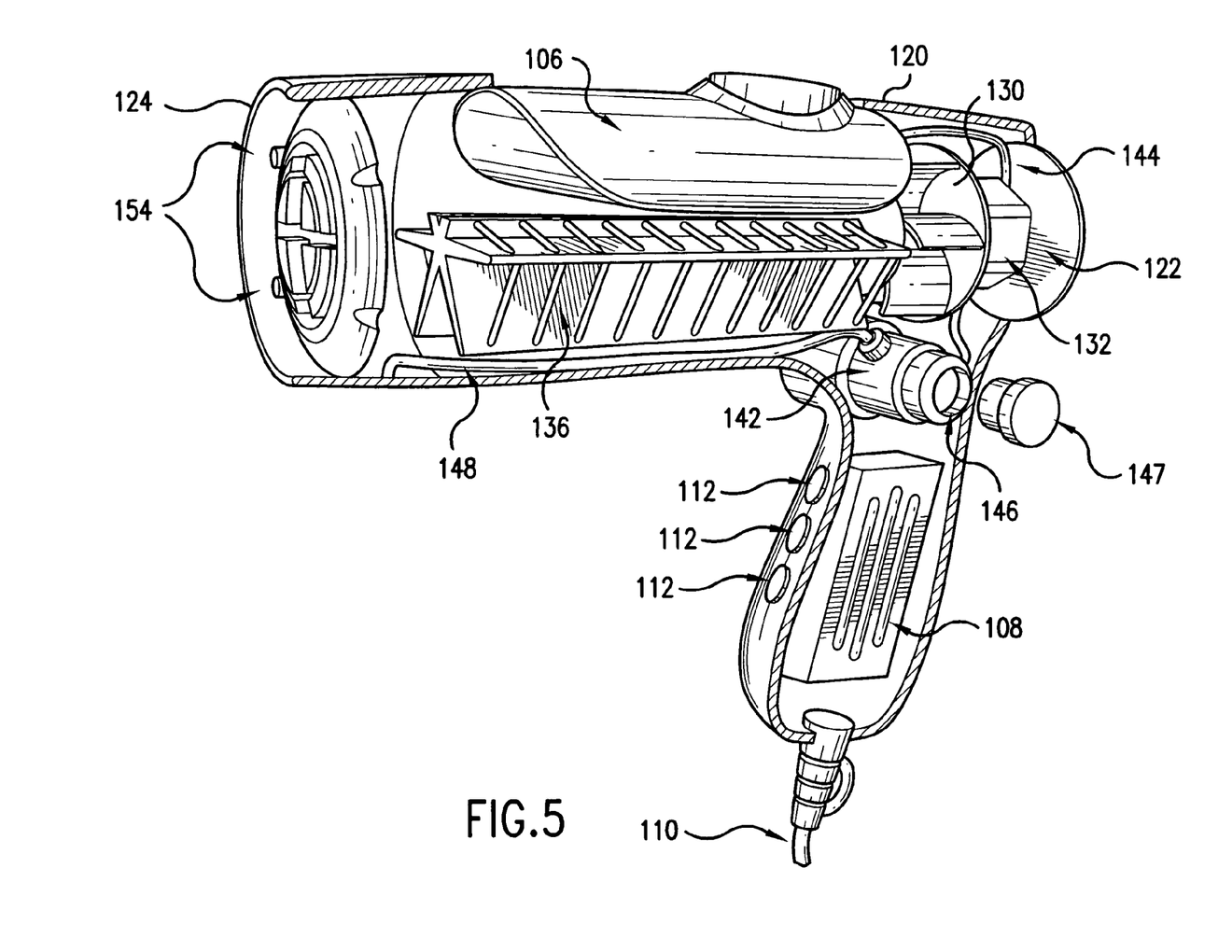
FIG. 5 is a cross-sectional view of the hair dryer assembly of FIG. 4.
Figure 6:
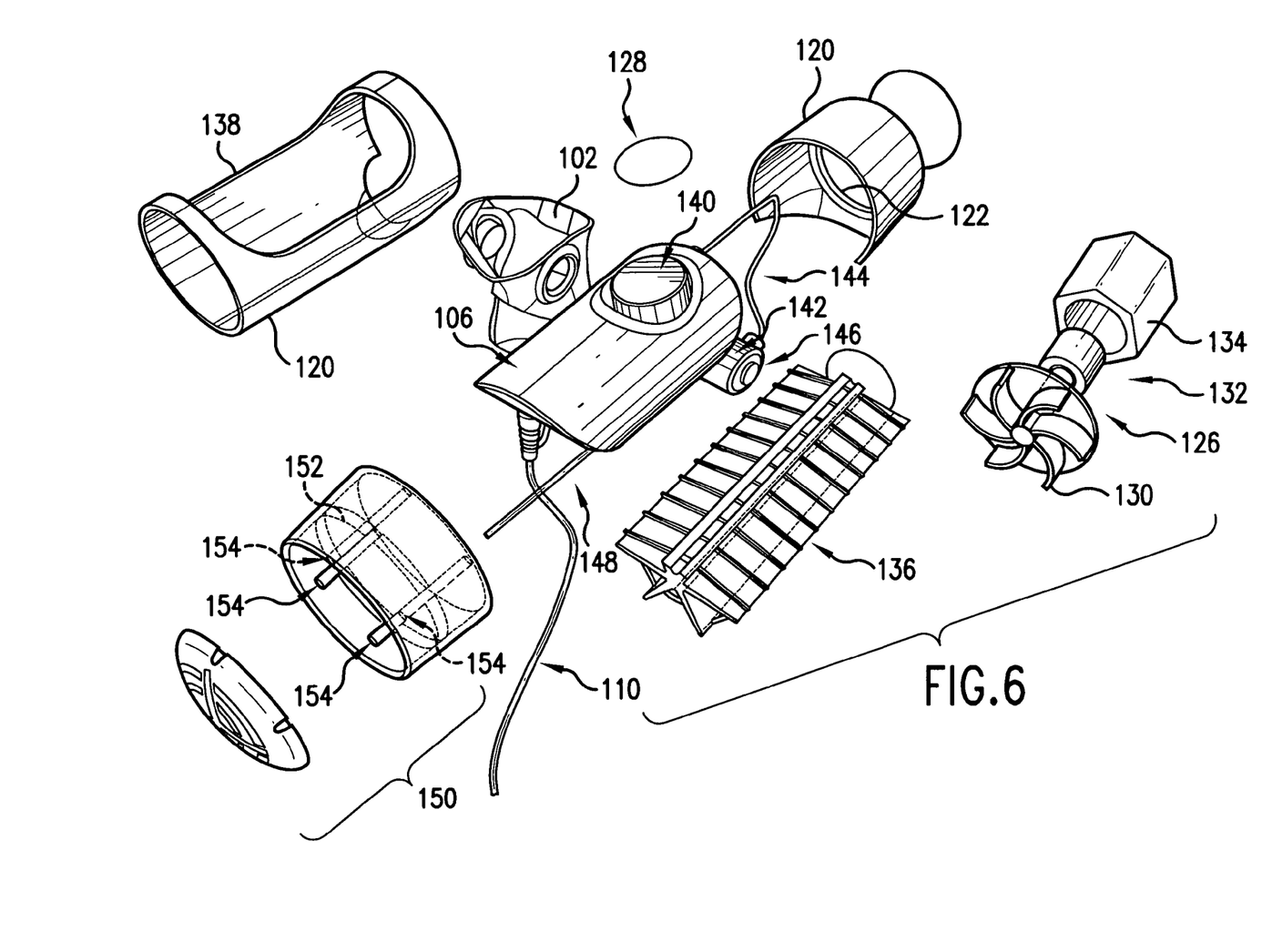
FIG. 6 is an exploded perspective view of the hair dryer assembly of FIG. 4.

FIGS. 4-6 illustrate one embodiment of a hair dryer assembly 100 according to the present invention. The hair dryer assembly 100 has a handle portion 102, a blower portion 104 and a water tank 106.

The handle portion 102 houses the electronics 108 for a conventional hair dryer. A power cord 110 extends from the handle portion 102 to supply external power to the hair dryer assembly 100. Switches 112 are provided on the handle portion 102 for controlling the hair dryer 100, including turning the hair dryer 100 on and off.

The blower portion 104 has a generally cylindrical housing 120 having an open rear end 122 and an open front end 124. A fan system 126, a heater 136 and a pump system are housed inside the housing 120. The fan system 126 is positioned adjacent the opening in the rear end 122, and includes a fan 130 carried on a shaft 132 extending from a motor 134 in a conventional manner well-known in the art. A heater 136 is positioned in front of the fan 130. The water tank 106 is positioned above the heater 136 through an opening 138 cut out of the housing 120. The water tank 106 has a water inlet 140 through which water can be introduced. A cover 128 blocks and secures the inlet 140. The pump system includes a sprayer 142 which is fluidly connected with the interior of the water tank 106 by a first tubing 144. The sprayer 142 is positioned between the heater 136 and the fan 130 adjacent the handle portion 102, and is coupled to a pump 146 that has a pump button 147 extending through the housing 120 for actuation and control by the user. The pump system further includes a spray mount 150 positioned adjacent the front end 124 and in front of the heater 136. A second tubing 148 extends below the heater 136 and fluidly connects the sprayer 142 and an internal conduit 152 provided in the spray mount 150. The internal conduit 152 is fluidly connected to a plurality of nozzles 154 through which water can be ejected. The pump 146 can be embodied in the form of any conventional negative-pressure pump, and functions to deliver water from the water tank 106 (via the tubings 144 and 148) to the spray mount 150.

The hair dryer assembly 100 can be used in the following manner. First, a switch 112 can be actuated to turn on the fan system 126 and the heater 136. The fan system 126 draws air through the opened rear end 122 and the fan 130 generates a flow of air that is directed towards the heater 136 and the front end 124 of the housing 120. The heater 136 generates heat to warm up the air that passes through the heater 136 from the fan 130 to the front end 124. The warmed air is blown out through the open front end 124. When the user desires to wet his or her hair, the user presses on the pump button 147, which creates negative pressure to draw water from the water tank 106 through the first tubing 144 to the sprayer 142 and pump 146, where the negative pressure further delivers the water through the second tubing 148 to the nozzles 154 (via the internal conduit 152 in the spray mount 150), where the water is ejected and sprayed. The water in the water tank 106 can be replenished by removing the cover 128 at the inlet 140 of the water tank 106.

FIGS. 7-10 illustrate one embodiment of a brush assembly 200 according to the present invention. The brush assembly 200 can be used as a conventional brush. The brush assembly 200 has a handle portion 202, a water tank 204, a water spray portion 206, and a brush portion BP1.

Figure 7:
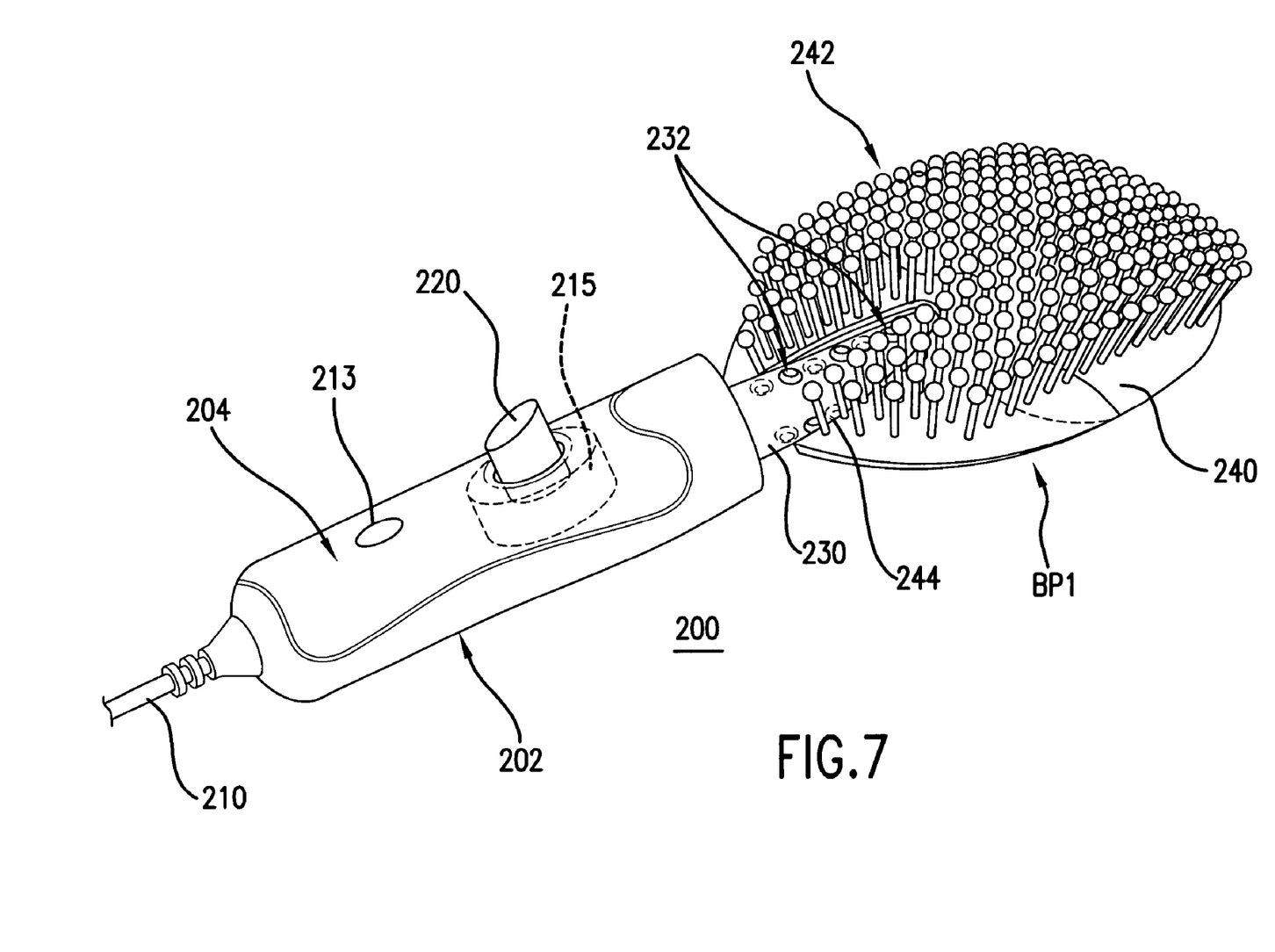
FIG. 7 is a perspective view of a brush assembly according to one embodiment of the present invention.
Figures 8, 9:
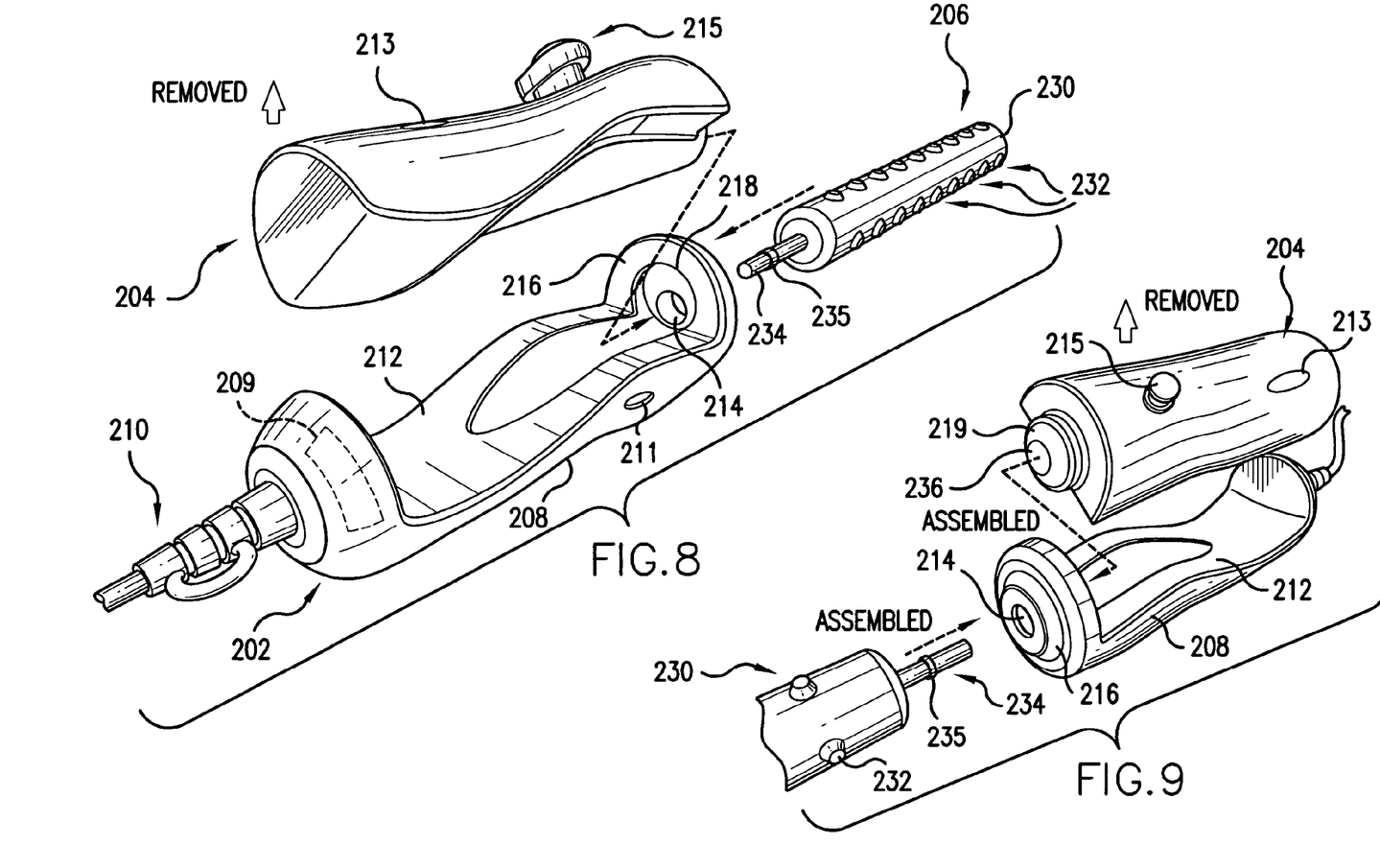
FIGS. 8 and 9 are two different exploded perspective view of the brush assembly of FIG. 7.

The handle portion 202 has an elongated housing 208 which houses the electronics (not shown) to power a heating element 209. A power cord 210 extends from the housing 208 to supply external power to the brush assembly 200. A switch 211 can be provided on the housing 208 for turning the heating element 209 on and off. If the brush assembly 200 is used as a conventional brush without the need for electrical power, the electronics, the heating element 209, the power cord 210 and the switch 211 can be omitted.

The housing 208 defines a cut-out region 212 which is adapted to receive the removable water tank 204. The water tank 204 can be fitted into the cut-out region 212, with the housing 208, the cut-out region 212 and the water tank 204 configured so that the entire handle portion 202 (with the water tank 204 attached thereto) has an ergonomically and aesthetically pleasing overall configuration. Aligned ridges (e.g., see 218, 219) can be provided on the housing 208 and the water tank 204 to secure the water tank 204 in the cut-out region 212. An opening 214 is provided at a front wall 216 of the housing 208. The water tank 204 has a cover 213 that closes the opening in the water tank 204 through which water is introduced.

A pump system 215 is provided in the water tank 204 to pump water from the inside of the water tank 204 to the water spray portion 206. A pump button 220 extends from the pump system 215 for the user to actuate the pump system 215.

The water spray portion 206 is fixedly secured to the brush portion BP1. The water spray portion 206 has an elongate tube 230 having a plurality of nozzles 232 provided in spaced-apart manner about the tube 230. A spray conduit 234 extends from one end of the tube 230 and is adapted to be fitted into the opening 214 in the front wall 216 of the housing 208 and through a water outlet 236 at one end of the water tank 204. A locking ring 235 can be provided on the conduit 234 to secure the conduit 234 at the opening 214.

The brush portion BP1 has a board 240 on which a plurality of bristles 242 are provided. The brush portion BP1 can be a brush portion for a conventional brush. The board 240 can assume any shape or size, and FIG. 7 illustrates the board 240 as having a generally oval shape. A slot 244 is provided along an edge of the board 240, and is adapted to receive, retain and expose a portion of the tube 230. In particular, the tube 230 is fixedly secured to board 240 at the location of the slot 244. The slot 244 also exposes a portion of the tube 230 (as best shown in FIG. 7) and some nozzles 232. Thus, water emitted through the nozzles 232 can exit through the slot 244.

Figure 10:
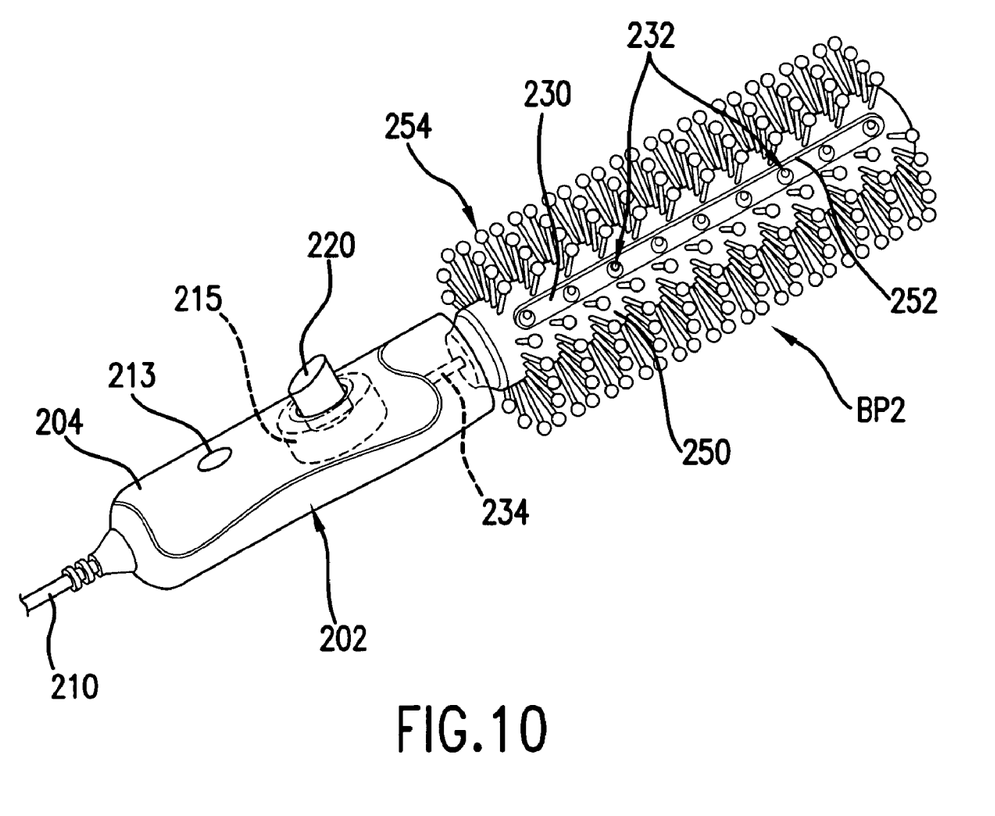
FIG. 10 illustrates the brush assembly of FIG. 7 in use with a different brush head.

The same handle portion 202 (and the water tank 204 carried thereon) can be used with a different brush portion, such as brush portion BP2 shown in FIG. 10. The brush portion BP2 can be a conventional curling brush, and has a tubular body 250 that defines an internal bore. The body 250 has at least one elongated slit 252 provided along the length thereof. A plurality of the nozzles 232 from the tube 230 are positioned along the slit 252. A plurality of bristles 254 are provided about the body 250. The tube 230 is adapted to be inserted into, and fixedly retained inside, the bore of the body 250.

To use the brush assembly 200 with brush portion BP1, the user grips the handle portion 202 to comb his or her hair, and if the user desires to spray a little water to his or her hair, the user presses the pump button 220, which causes water from the water tank 204 to be delivered via the outlet 236 and the conduit 234 to the tube 230 and ejected through the nozzles 232. If a heating element 209 is provided, the user can turn on the switch 211 to turn on the heating element 209, which will warm up the water retained inside the water tank 204, so that the ejected water can be warm.

To use the brush assembly 200 with brush portion BP2, the user grips the handle portion 202 to comb his or her hair, and if the user desires to spray a little water to his or her hair, the user presses the pump button 220, which causes water from the water tank 204 to be delivered via the outlet 236 and the conduit 234 to the tube 230 and ejected through the nozzles 232 and the slit 252. If a heating element 209 is provided, the user can turn on the switch 211 to turn on the heating element 209, which will warm up the water retained inside the water tank 204, so that the ejected water can be warm.

While the description above refers to particular embodiments of the present invention, it will be understood that many modifications may be made without departing from the spirit thereof.

What is claimed is:

1. A heater assembly, comprising:
   a water tank that contains water;
   a blower portion having a housing, and air outlets provided on the housing through which air from the blower portion is directed into the environment, the blower portion further including a heater and a blower housed inside the housing;
   a humidifier portion directly mounted to the housing, the humidifier portion including a water tank and having a fan that is separate from the blower portion, and mist outlets through which mist is directed into the environment; and
   wherein the blower portion further includes water outlets coupled via a conduit to the water tank for dispensing water into the environment, and wherein the mist outlets and the air outlets are separate from the water outlets.

2. The assembly of claim 1, wherein the housing houses a motor, and wherein the water outlets are provided on the housing.

3. The assembly of claim 1, further including a pump that delivers water from the water tank to the water outlet.

4. A heater assembly, comprising:
   a blower portion having a housing having air outlets through which air from the blower portion is directed into the environment, the blower portion further including a motor, a blower, and a heater that are housed inside the housing, and water outlets;
   a humidifier portion directly mounted to the housing and having a water tank, the humidifier portion having a fan that is separate from the blower portion, and mist outlets through which mist is directed into the environment, with the mist outlets and air outlets being separate from the water outlets;
   wherein the water outlets are coupled to the water tank via a conduit for dispensing water into the environment; and
   a pump that delivers water from the water tank to the water outlet.

* * * * *